United States Patent
Lee et al.

(10) Patent No.: US 11,525,830 B2
(45) Date of Patent: Dec. 13, 2022

(54) BIOSENSOR FOR DETECTING INFLUENZA A VIRUS USING AU—FE₃O₄ COMPOSITE

(71) Applicant: Ji Hoon Lee, Gaithersburg, MD (US)

(72) Inventors: Ji Hoon Lee, Gaithersburg, MD (US); Carol T. Lee, Gaithersburg, MD (US)

(73) Assignee: Ji Hoon Lee, Gaithersburg, MD (US)

( * ) Notice: Subject to any disclaimer, the term of this patent is extended or adjusted under 35 U.S.C. 154(b) by 184 days.

(21) Appl. No.: 16/755,805

(22) PCT Filed: Oct. 15, 2018

(86) PCT No.: PCT/US2018/055893
§ 371 (c)(1),
(2) Date: Apr. 13, 2020

(87) PCT Pub. No.: WO2019/075467
PCT Pub. Date: Apr. 18, 2019

(65) Prior Publication Data
US 2021/0270833 A1    Sep. 2, 2021

Related U.S. Application Data

(60) Provisional application No. 62/572,293, filed on Oct. 13, 2017.

(51) Int. Cl.
*G01N 33/569* (2006.01)
*G01N 33/553* (2006.01)
*G01N 33/58* (2006.01)

(52) U.S. Cl.
CPC ..... *G01N 33/56983* (2013.01); *G01N 33/553* (2013.01); *G01N 33/582* (2013.01); *G01N 2333/11* (2013.01)

(58) Field of Classification Search
None
See application file for complete search history.

(56) References Cited

U.S. PATENT DOCUMENTS

2011/0129816 A1\* 6/2011 Muraguchi ...... G01N 33/56983
435/5

\* cited by examiner

*Primary Examiner* — Shanon A. Foley
*Assistant Examiner* — Myron G Hill
(74) *Attorney, Agent, or Firm* — Dentons US LLP

(57) ABSTRACT

A biosensor for detecting an influenza A virus in a sample is disclosed, which includes: an influenza A virus antibody immobilized on a surface of Au—Fe₃O₄ composite; where the antibody binds with the influenza A virus in the sample, which converts 4-methylumbelliferyl-N-acetyl-α-D-neuraminic acid (MUNANA) to 4-methylumbelliferone (4-MU), where the 4-MU emits green light at pH of 5.5-6.5; and wherein the 4-MU emits blue light at pH of 9.3-11.3. In the biosensor, 1,1'-oxalyldiimidazole chemiluminescence (ODI-CL) reagent may be utilized to emit the blue and green lights.

8 Claims, 8 Drawing Sheets

(A)  (B)

(A)  (B)

BIOSENSOR FOR DETECTING INFLUENZA A VIRUS USING AU—FE₃O₄ COMPOSITE

This application is a 35 USC § 371 National Stage entry of International Application No. PCT/US2018/055893, filed on Oct. 15, 2018, which claims priority to U.S. Provisional Application No. 62/572,293, filed on Oct. 13, 2017, all of which are incorporated by reference in their entirety herein.

TECHNICAL FIELD

The present disclosure relates to a biosensor and a method for detecting an influenza. A virus in a sample. According to the biosensor of the present disclosure, it is possible to provide a cost-effective and rapid enzyme immunoassay for influenza A virus. The present disclosure also provides highly sensitive analytical method capable of accurately and selectively quantifying influenza A viruses.

BACKGROUND ART

The flu, which is caused by various influenza viruses, is a contagious respiratory illness. Most people with an influenza virus infection have mild symptoms and can recover within two weeks. However, in serious cases, which are likely to occur in children under the age of 5, adults over the age of 65, pregnant women, and people who have medical conditions, patients are likely to either be hospitalized or even die.

The major types of influenza viruses that routinely spread among people are influenza A and B viruses. Influenza A viruses are classified according to 15 different hemagglutinin (HA) subtypes and 9 different neuraminidase (NA) subtypes while influenza B virus is not divided into subtypes. Various types of influenza A viruses created by many different combinations of HA and NA proteins have been reported. It is well-known that influenza A viruses such as H1N1, H1N2, and H3N2 commonly infect people. In fact, the Centers for Disease and Control and Prevention (CDC) reported that the first global influenza pandemic was caused by influenza A (H1N1) virus (https://www.cdc.gov/flu/about/season/flu-season-2017-2018.htm).

It is difficult to diagnose a specific type of influenza A virus based on only the symptoms. Thus, various methods for the diagnosis of specific influenza A viruses have been developed. The sandwich enzyme immunoassays (EIA) with two antibodies are capable of selectively capturing a specific type of influenza A virus. Currently, electrochemical and optical sensors such as chemiluminescence, colorimetric, and fluorescence are widely applied as a detection method of sandwich EIA operated with a capture antibody and a detection antibody conjugated with horseradish peroxidase (HRP) or alkaline phosphatase (AP). In order to rapidly analyze influenza A viruses with high sensitivity and selectivity, EIAs using nanoparticles, such as gold, platinum, silver, and magnetic beads have been developed. However, Most of EIAs reported so far are complicated, expensive, and time-consuming.

As shown in FIG. 1, neuraminidase (NA), a subtype of influenza A virus, can be applied as an enzyme to devise biosensors with fluorescence detection. 2'-(4-Methylumbelliferyl)-α-D-N-acetylneuraminic acid (MUNANA), a fluorogenic substrate, is converted to 4-methyllumbelliferone (4MU) in the presence of NA at acidic condition (pH 4.5-6). The concentration of 4MU formed in this reaction is dependent on the concentration of NA in a sample containing influenza A virus. In other words, the fluorescence intensity of 4MU formed from the reaction of NA and MUNANA (see FIG. 1) is proportionally enhanced with the increase of NA in a sample. 4MU excited at 365 nm emits blue light at 450 nm. Biosensors devised using the scheme in FIG. 1 were applied for the quantitative and qualitative analyses of influenza A viruses. However, it was not possible to detect a specific type of influenza A virus in a sample because the biosensors were operated without any antibodies capable of selectively capturing a specific type of influenza A virus.

Therefore, a biosensor and a method which can effectively and rapidly detect a specific type of influenza A virus in a sample have yet to be developed.

SUMMARY

According to one aspect of the present invention, a biosensor for detecting an influenza. A virus in a sample is provided, which comprises: an influenza A virus antibody immobilized on a surface of Au—Fe₃O₄ composite; wherein the antibody binds with the influenza A virus in the sample, which converts 4-methylumbelliferyl-N-acetyl-α-D-neuraminic acid (MUNANA) to 4-methylumbelliferone (4-MU), wherein the 4-MU emits green light at pH of 5.5-6.5; and wherein the 4-MU emits blue light at pH of 9.3-11.3. In the biosensor, 1,1'-oxalyldiimidazole chemiluminescence (ODI-CL) reagent may be utilized to emit the blue and green lights. The 1,1'-oxalyldiimidazole chemiluminescence (ODI-CL) reagent may comprise an ODI and $H_2O_2$. The sample may be plasma or whole blood.

In accordance with another aspect of the present invention, a kit for detecting an influenza A virus in a sample is provided, the kit comprises: the above biosensor; and a container. The kit may further comprise: a sodium phosphate buffer for adjusting the pH between 5.5 to 6.5; a sodium hydroxide buffer for adjusting the pH between 9.3-11.3; and 1,1'-oxalyldiimidazole chemiluminescence (ODI-CL) reagent. The 1,1'-oxalyldiimidazole chemiluminescence (ODI-CL) reagent may comprise an ODI and $H_2O_2$.

In yet another aspect of the present invention, a method of detecting an influenza A virus in a sample is provided, the method comprises: immobilizing an influenza A virus antibody on a surface of Au—Fe₃O₄ composite; mixing the immobilized antibody with 4-methylumbelliferyl-N-acetyl-α-D-neuraminic acid (MUNANA), and incubating the mixture to form 4-methylumbelliferone (4-MU); adjusting pH of the incubated mixture between 5.5 to 6.5 and measuring light intensity derived from the 4-MU by using a first enzyme assay with 1,1'-oxalyldiimidazole chemiluminescence (ODI-CL) detection; and adjusting pH of the incubated mixture between 9.3-11.3 and measuring light intensity of derived from the 4-MU by using a second enzyme assay with 1,1'-oxalyldiimidazole chemiluminescence (ODI-CL) detection. In this method, a sodium phosphate buffer may be used for adjusting the pH between 5.5 to 6.5; and a sodium hydroxide buffer may be used for adjusting the pH between 9.3-11.3. The first and second enzyme assays with 1,1'-oxalyldiimidazole chemiluminescence (ODI-CL) detection may be performed by using ODI and $H_2O_2$. The influenza A virus antibody may be a hemagglutinin (HA) subtype antibody. The influenza A virus may be H1N1 type, 1-T3N2 type or H5N1 type influenza A virus. The above step of incubating the mixture may be performed for 6-12 minutes at room temperature.

These and other aspects will be appreciated by one of ordinary skill in the art upon reading and understanding the following specification.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION

The high-energy intermediate (X) formed in 1,1'-Oxalyldiimidazole chemiluminescence (ODI-CL) reaction acts as a light source of fluorescence like a laser or Xenon lamp. This is because X can transfer energy to a fluorescent compound on the basis of the principle of internal chemiluminescence resonance energy transfer (CRET). The fluorescent compound after the internal CRET emits bright CL emission. It is well-known that ODI-CL with low background noise is more sensitive than fluorescence operated with high-voltage power supply to operate a laser or Xenon lamp.

Figure 1:
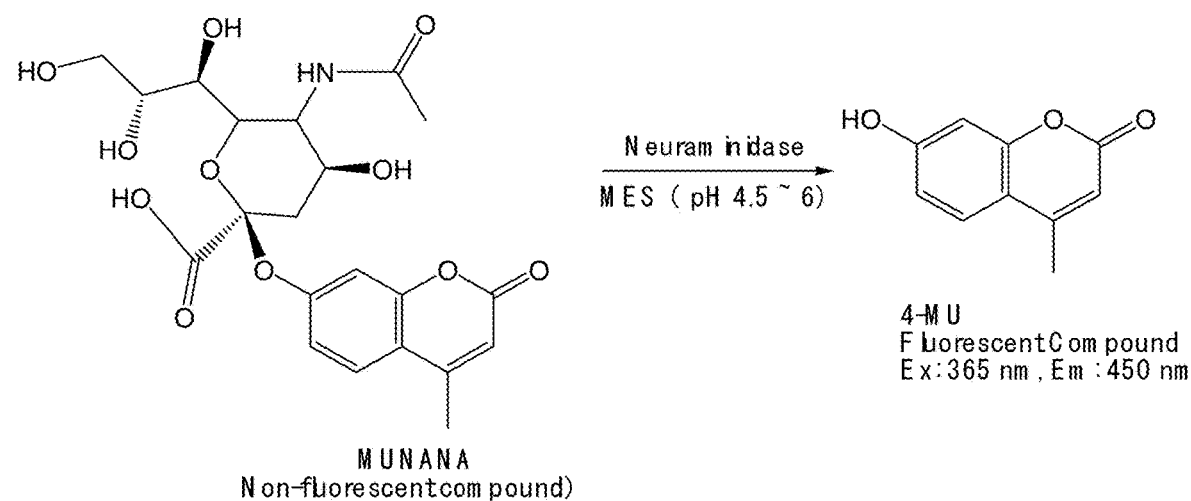
FIG. 1 shows the reaction mechanism of MUNANA and NA to produce 4 MU.
Figure 2:
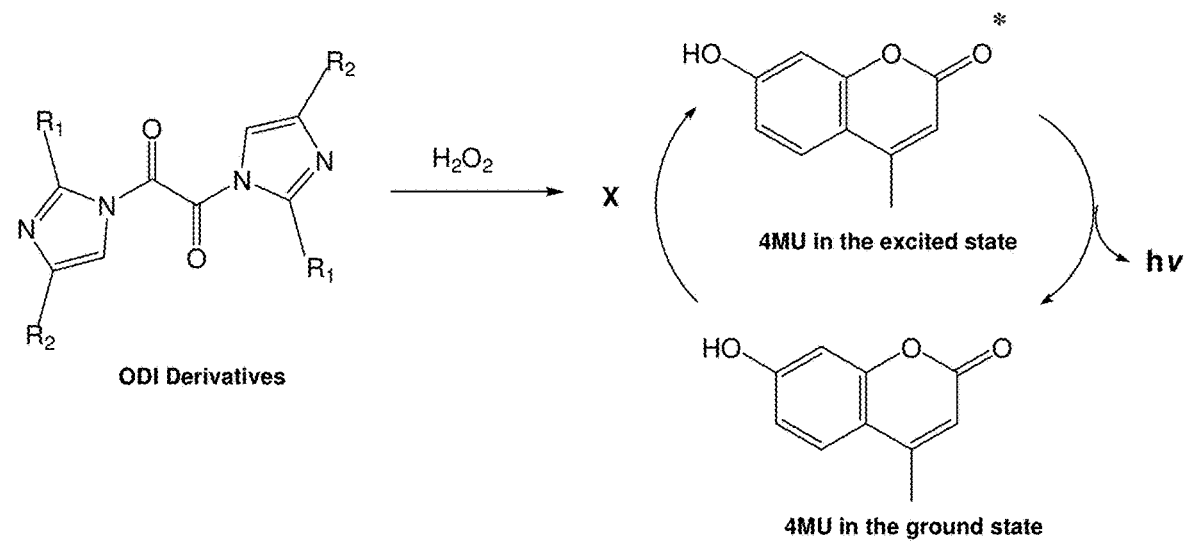
FIG. 2 shows the reaction mechanism of ODI-CL for the detection of 4MU. ($R_1$ and $R_2$ is H, $CH_3$, or $CH_2CH_3$. X is the high-energy intermediate formed from the reaction of ODI derivatives and $H_2O_2$.)

Based on the advantages of ODI-CL detection, the inventor of the present invention found that, the quantum efficiency of the light emitted from 4 MU in ODI-CL reaction is as good as that of 4MU fluorescence, and thus, ODI-CL detection can be applied to detect trace levels of 4MU based on the reaction mechanism shown in FIG. 2. Thus, ODI-CL detection can quantify the concentration of NA in a sample containing influenza A viruses with the combination of the schemes in FIG. 1 and FIG. 2. The inventor of the present invention also found that when 4MU formed from the reaction of MUNANA and NA is detected, it is possible to quantify trace levels of NA in a sample containing influenza A viruses. In order to selectively quantify a specific influenza A virus in a sample, it is necessary to develop an enzyme immunoassay.

As the NA, the subtype of the influenza A, may work as an enzyme, and trace levels of NA in a sample can be quantified, the inventor of the present invention also found that the NA of influenza A virus bound with a capture antibody is still active as an enzyme, and it thus, is possible to develop a cost-effective and rapid enzyme immunoassay with ODI-CL detection using only capture antibody without a detection antibody.

According to an embodiment of the present invention, a biosensor for detecting an influenza A virus in a sample is provided, where the biosensor comprises an influenza A virus antibody immobilized on a surface of Au—$Fe_3O_4$ composite material. According to certain embodiments, the Au—$Fe_3O_4$ composite material can be characterized as a nanocomposite, due to the size of the constituents of the composite material. The antibody bound with the influenza A virus may convert 4-methylumbelliferyl-N-acetyl-α-D-neuraminic acid (MUNANA) to 4-methylumbelliferone (4-MU), wherein the 4-MU emits green light at pH of 5.5-6.5; and wherein the 4-MU emits blue light at pH of 9.3-11.3.

According to an embodiment of the present invention, the biosensor may utilize 1,1'-oxalyldiimidazole chemiluminescence (ODI-CL) detection method for rapidly monitoring influenza A viruses such as H1N1, H3N2, and H5N1. In this specification, H1N1 is used as an example, but other NA subtype may be used.

A specific antibody, capable of capturing H1N1, may be immobilized on the surface of the gold (Au)-iron ($Fe_3O_4$) nanocomposite. A standard or sample mixed with Au—$Fe_3O_4$ nanocomposites may be incubated (e.g., for 1 hr at 37° C.), and then, the Au—$Fe_3O_4$ nanocomposites can be washed 3 times using PBST. Then, 4-Methylumbelliferyl-N-acetyl-α-D-neuraminic acid (MUNANA, 100 μl), a fluorogenic substrate of neuraminidase, may be added and incubated for 6-12 minutes (preferably, 8-10 minutes) to produce 4-Methylumbelliferone (4-MU) from the reaction between MUNANA and neuraminidase of H1N1. After the incubation, the solution containing 4-MU transferred into a borosilicate test tube may emit bright light when $H_2O_2$ and ODI were consecutively added into the test tube. The inventor of the present invention found that the relative CL intensity of 4MU was proportionally enhanced with the increase of H1N1. Additionally, the biosensor according to an embodiment of the present invention is accurate, precise, and has good reproducibility, as well as excellent selectivity. The biosensor using Au—$Fe_3O_4$ nanocomposites can be applied as a cost-effective and rapid method capable of selectively quantifying just one specific type among the various types of influenza A viruses in a sample.

The sample may be plasma or whole blood, but the present invention is not limited to the type of the sample. The influenza A virus antibody may be a hemagglutinin (HA) subtype antibody. The influenza A virus may be H1N1 type, H3N2 type or H5N1 type influenza A virus.

A biosensor as described above may be provided in the form of a kit. In one embodiment of the present invention, the kit includes the above-described biosensor and a container. The kit may further include a buffer and an ODI-CL reagent (e.g., ODI and $H_2O_2$). As the buffers, a sodium phosphate buffer can be used for adjusting the pH between 5.5 to 6.5 and a sodium hydroxide buffer can be used for adjusting the pH between 9.3-11.3.

Hereinafter, embodiments will be explained in detail to particularly explain the present invention. The present invention may, however, be embodied in different forms and should not be construed as limited to the embodiments set forth herein. Rather, these embodiments are provided so that this disclosure will be thorough and complete, and will fully convey the scope of the inventive concept to those skilled in the art.

Experiment 1: Enzyme Assay with ODI-CL Detection

MUNANA (0.5 mM, 100 μl) was mixed with an influenza A virus recombinant (100 μl) such as H1N1, H3N2, or H5N1 at room temperature. The mixture was incubated for 10 min at room temperature. 4MU was formed from the enzyme reaction of MUNANA and NA of influenza A virus. 4MU (10 μl) transferred into a borosilicate test tube was inserted into a luminometer with two dispensers (Lumat 9507, Berthold, Inc). $H_2O_2$ (25 μl) in isopropyl alcohol was injected into the test tube through the first dispenser. Then, CL emission of 4MU was measured immediately for 2 sec after injecting ODI (25 μl) into the test tube through the second dispenser.

Experiment 2: Optimization of Buffer Solution for the Detection of 4MU in ODI-CL Reaction 4MU formed from the reaction of NA and MUNANA in MES buffer as shown in FIG. 1 has been quantified with fluorescence detection. Thus, the inventor of the present invention tested whether 4MU in MES buffer can emit bright light in ODI-CL reaction based on FIG. 2. Unfortunately, as shown in FIG. 3(A), 4MU in MES buffer emits dim light in ODI-CL reaction even though the relative CL intensity at pH 6.5 was about 3-fold stronger than that at pH 5.5. FIG. 3(A) indicates that MES may not be an appropriate buffer for the analysis of 4MU using ODI-CL detection.

As shown in FIG. 3(B), it is confirmed that CL emission of 4MU in sodium phosphate buffer (pH 6) is about 100-fold brighter than that in MES buffer (pH 6). Also, the relative CL intensity of 4MU under the basic condition was stronger than that at pH 6. The strongest CL emission of 4MU was observed at pH 10.9. Then, CL emission measured in more basic condition than pH 10.9 was decreased. Based on the results shown in FIG. 3(C), the appropriate pH range of sodium phosphate is expected to be 9.3-11.3 for the measurement of strong emission of 4MU in ODI-CL reaction.

FIG. 3(D) shows that the color of light emitted from 4MU in ODI-CL reaction is dependent on pH of sodium phosphate buffer. The color of light emitted at pH 6 is green, whereas the bright blue light emitted at pH 10.1 was observed. The results indicate that the CL emission at pH 10.1 was enhanced with the blue-shift of CL wavelength.

Figure 3:
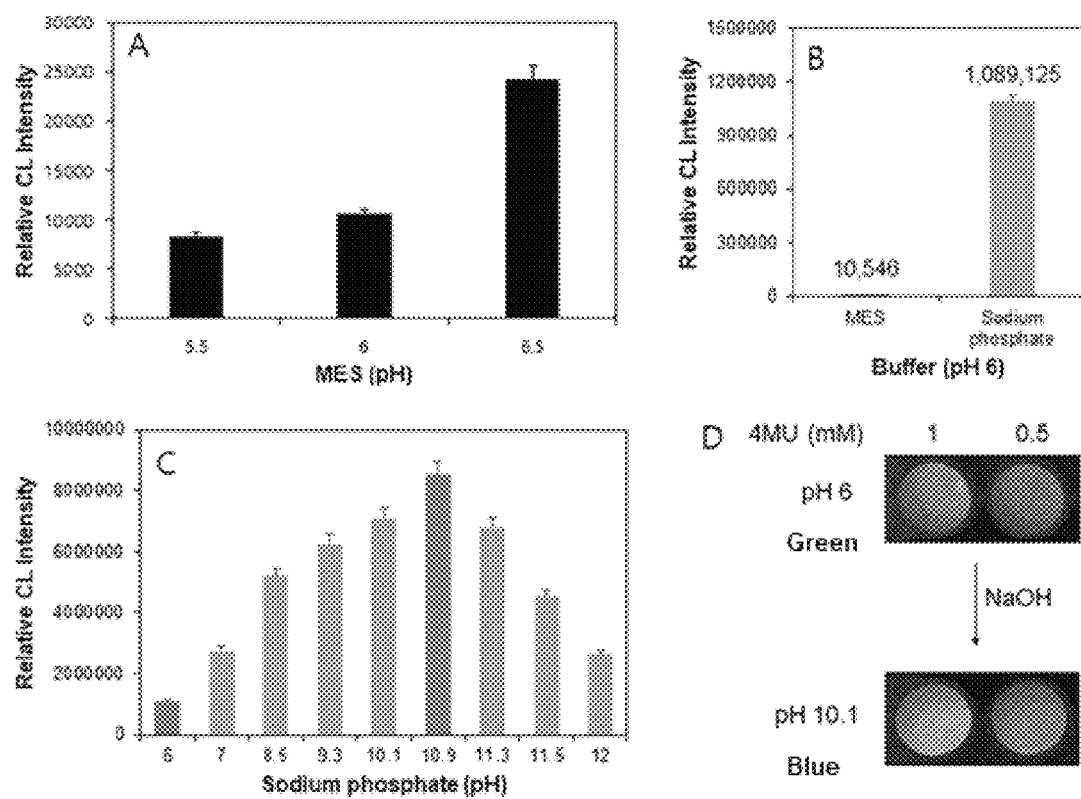
FIG. 3 shows (A) pH effect of MES buffer in the presence of 4MU (10 μM), (B) Components effect of buffer solution in the presence of 4MU (10 μM), (C) pH effect of sodium phosphate buffer in the presence of 4MU (10 μM), (D) Color change of 4MU emitted in ODI-CL reaction under the acidic (pH 6) and the basic (pH 10.1) conditions.
Figure 4:
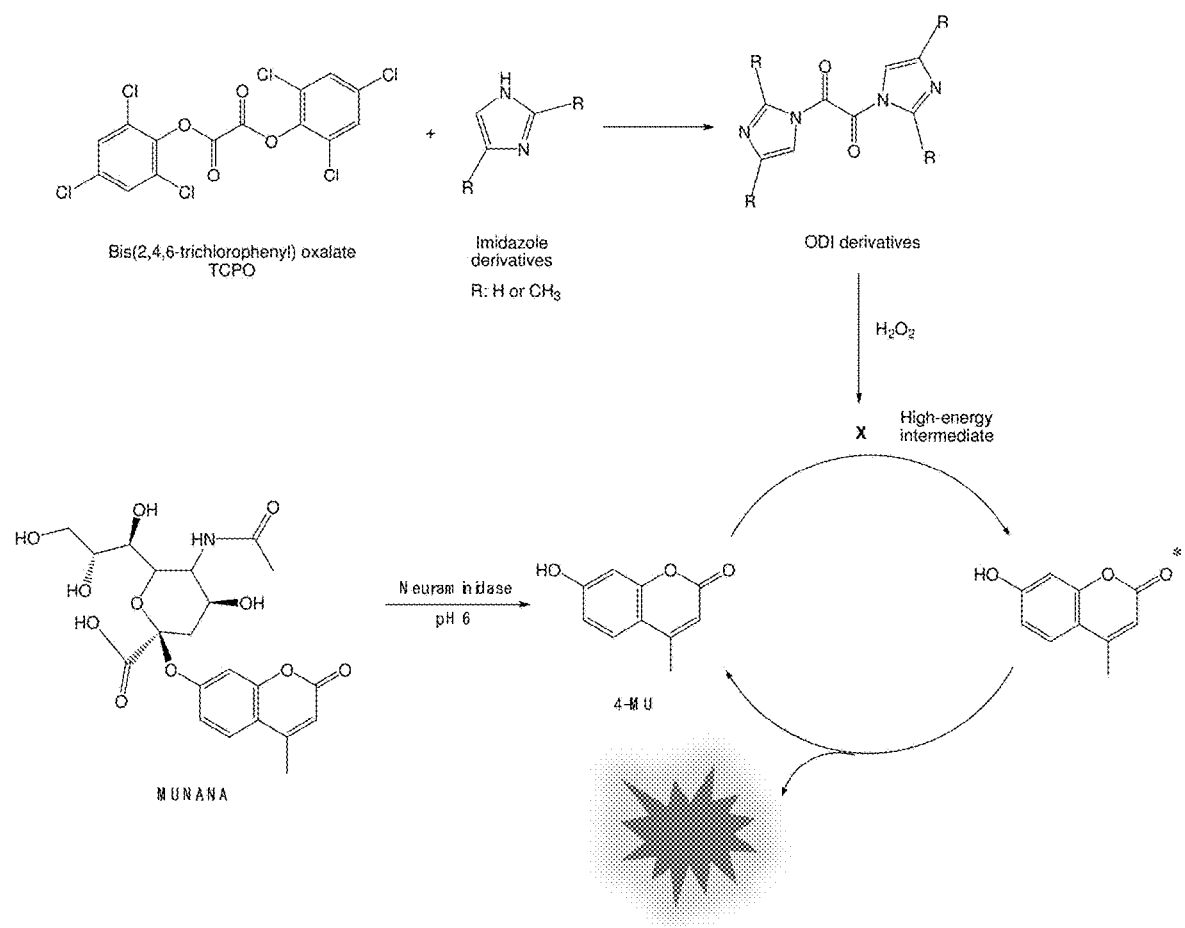
FIG. 4 shows the reaction mechanism for the quantification of 4MU formed from the reaction of NA and MUNANA using ODI-CL detection. ($R_1$ and $R_2$ are H, $CH_3$, or $CH_2CH_3$.)

Based on the results shown in FIG. 3, it is confirmed that ODI-CL detection can detect trace levels of 4MU.

Experiment 3: Reaction of NA and MUNANA in Phosphate Buffer and Detection of 4MU in ODI-CL Reaction Based on the results of FIG. 3 and the combination of the schemes in FIGS. 1 and 2, the reaction mechanism (FIG. 4) for the detection of 4MU formed from the reaction between NA and MUNANA using ODI-CL detection is developed.

FIG. 5(A) shows that the reaction rate of NA and MUNANA to produce 4MU is dependent on the pH of sodium phosphate. The reaction of NA and MUNANA at pH 6 ended after 20 min, whereas the reaction at pH 7 was not yet finished at 60 min. The results indicate that the reaction of NA and MUNANA in acidic condition (e.g., pH of 5.5-6.5) may be faster than that in neutral condition.

After the reaction of NA and MUNANA at pH 6, a different concentration of NaOH was added into the solution. The volume ratio between NaOH and the solution after the reaction was 1:9. As shown in FIG. 5(B), the relative CL intensity of 4MU was enhanced when a certain concentration of NaOH was added in the solution. The highest CL intensity of 4MU was measured with the addition of 125 mM NaOH. Thus, the final concentration of NaOH in the mixture was 12.5 mM. The pH of the mixture was 10.1. In the presence of higher NaOH than 12.5 mM, the strength of CL emission was decreased because pH of the mixture was higher than pH 11. As shown in FIG. 5(C), the color of the light emitted from 4MU formed from the reaction of NA and MUNANA was changed from green ($1^{st}$, $2^{nd}$, $3^{rd}$ photos from left) to blue ($4^{th}$ photo from left) due to the blue-shift of the emission wavelength. The result of FIG. 5(C) indicates that the emission wavelength of 4MU in ODI-CL reaction is dependent on the pH of solution for the reaction between MUNANA and NA.

Figure 6:
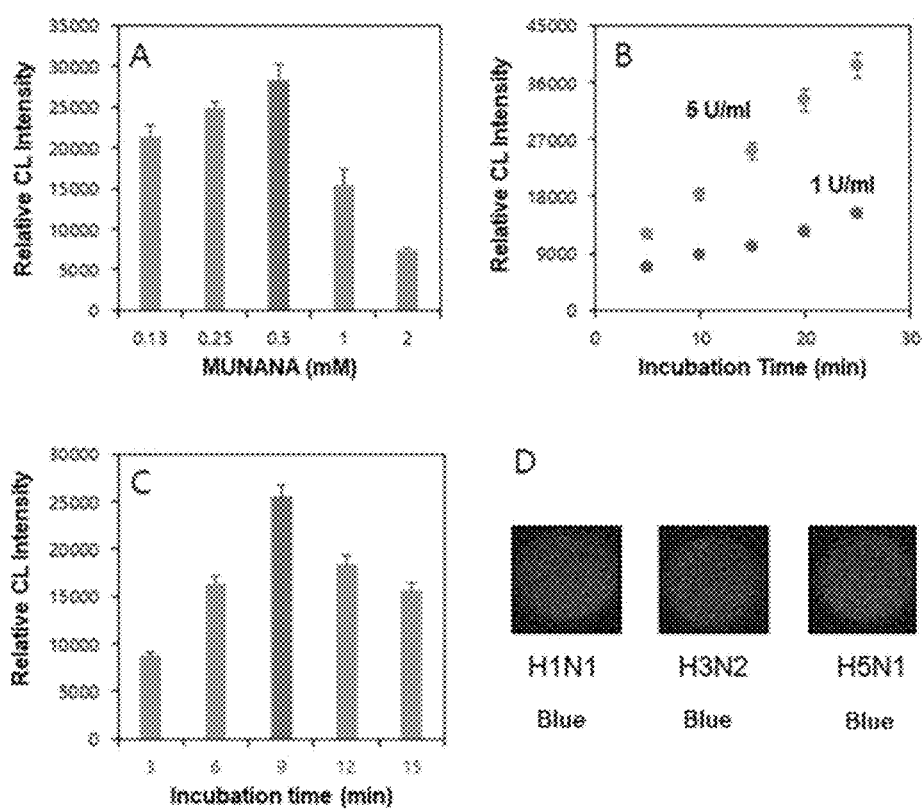
FIG. 6 shows (A) Effect of MUNANA concentration to measure the CL of 4MU formed from the reaction H1N1 (5 U/ml) and MUNANA for 10 min at room temperature, (B) Effect of incubation time for the reaction of H3N2 and MUNANA (0.5 mM) at room temperature, (C) Effect of incubation time for the reaction of H5N1 and MUNANA (0.5 mM) at room temperature, (D) CL of 4MU at pH 10.1. 4MU was formed from the reaction of influenza A virus (20 U/ml) and MUNANA (5 mM) for 10 min at room temperature. After the reaction, NaOH was added to stop the reaction and to enhance CL emission of 4MU. The pH of the mixture was 10.1.

FIG. 6 (A) indicates that the best concentration of MUNANA may be 0.5 mM for the reaction with H1N1 to produce 4MU. The relative CL intensity in the presence of higher MUNANA than 0.5 mM was decreased due to the self-quenching of relatively excess 4MU formed from the reaction of H1N1 and MUNANA (>0.5 mM).

FIG. 6(B) shows that the incubation time to maximize the yield of 4MU from the reaction of H3N2 and MUNANA (0.5 mM) is longer than that from the reaction of H1N1 (or H5N1) and MUNANA. The results indicate that the incubation time of influenza A virus and MUNANA may be proportionally extended with the increase of NA number of influenza A virus subtype.

FIG. 6(C) shows that the best incubation time to measure the highest CL intensity in the presence of H5N1 (5 U/ml) is 6-12 minutes (preferably 8-10 minutes, most preferably 9 minutes). With the increase of the incubation time, the relative CL intensity was quenched.

4MU was formed from the reaction of influenza A virus and MUNANA for 10 min at pH 6. Then, NaOH was added in the solution to stop the reaction. As shown in FIG. 6(D), 4MU at pH 10.1 emitted blue light.

Figure 5:
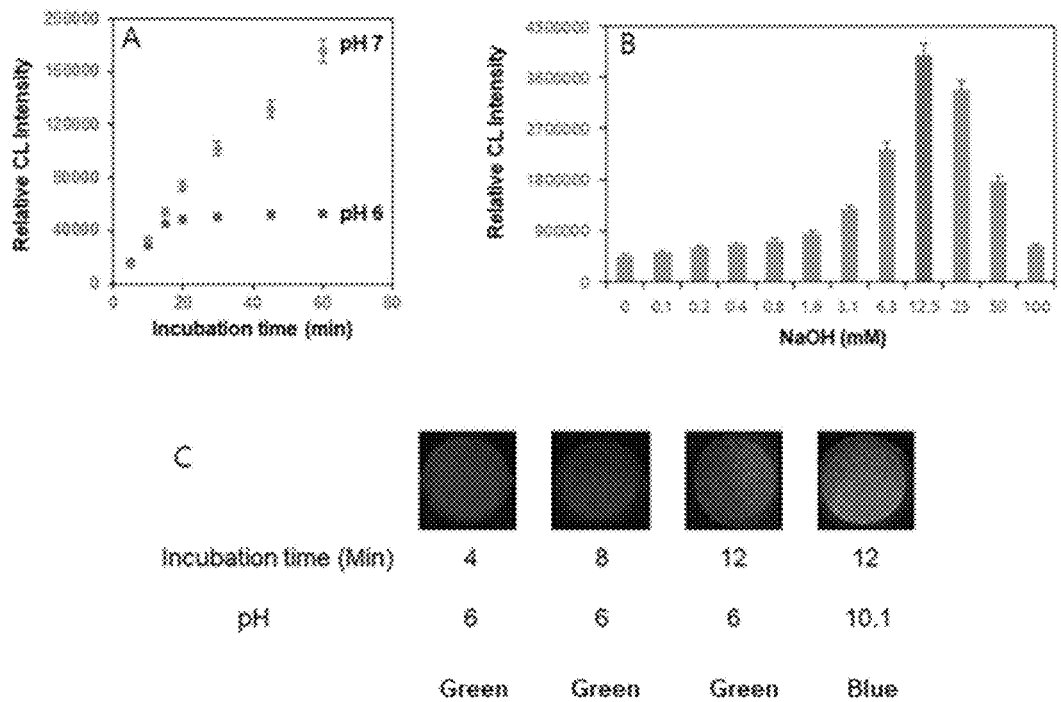
FIG. 5 shows (A) Effect of pH in the reaction of NA and MUNANA, (B) Concentration effect of NaOH added in the solution after the reaction of NA and MUNANA at pH 6. (C) CL emission of 4MU formed from the reaction of NA and MUNANA at pH 6 and 10.1.

Based on the experimental results shown in FIGS. 5 and 6, it is confirmed that ODI-CL detection can quantify trace levels of NA in a sample containing influenza A virus. Thus, a cost-effective and rapid enzyme immunoassay for the detection of a specific type of influenza A virus in a sample can developed.

EXAMPLES

The experiments described in this specification were conducted with the following materials and procedures.

Chemical and Materials

Recombinant proteins of influenza A H1N1 (100 U), H3N2 (80 U), and H5N1 (60 U) with NA activity were purchased from SINO Biological. Goat polyclonal influenza A antibody (H1N1) was purchased from Fitzgerald. 2'-(4-Methylumbelliferyl)-α-D-N-acetylneuraminic acid (MU-NANA), 4-methyllumbelliferone (4MU), Neuraminidase (6 U) from Clostridium perfringens (C. welchii), bovine serum albumin, horseradish peroxidase (HRP), iron (III) chloride, iron(II) chloride, ammonium hydroxide ($NH_3OH$, 28% $NH_3$ in $H_2O$)) and 30% hydrogen peroxide were purchased from Sigma-Aldrich. Bis(2,4,6-trichloro)phenyl oxalate (TCPO), 4-methyl imidazole, were purchased from TCI America. Au nanoparticles (14 nm, 1000 ppm) were purchased from US Research Nanomaterials. Ethyl acetate (Spectroscopic grade) and Isopropyl alcohol were purchased from EMD. Sodiun hydroxide (NaOH, 1 N) and sodium phosphate buffer (pH 6 and 7) were purchased from VWR. Amplex Red was purchased from ThermoFisher Scientific. Deionized water (18 MΩ) was used for the research.

Syntheses of $Fe_3O_4$ Nanoparticles and Au—$Fe_3O_4$ Nanocomposites

The mixture of $FeCl_3$ (20 mg) and $FeCl_2$ (5 mg) in 1ml deionized water was transferred into a 1.5-ml microcentrifuge tube. The microcentrifuge tube was inserted into a Micro Centrifuge Tube Thermomixer (Eppendorf) and shaken at 500 rpm for 10 sec at 85° C. Then, ammoniumhydroxide (20 μl,) was dispensed into the microcentrifuge. The microcentrifuge tube in the thermomixer was shaken at 1500 rpm for 1 hr at 85° C. $Fe_3O_4$ formed in the microcentrifuge tube was cooled at room temperature. Then, $Fe_3O_4$ was washed in water using a magnetic separator. $Fe_3O_4$ nanoparticles were stored in a refrigerator.

The mixture (0.5 ml) of $FeCl_3$ (20 mg/ml) and $FeCl_2$ (5 mg/ml) in deionized water was added in a 1.5-ml microcentrifuge tube containing Au nanoparticles (100 ppm, 14 nm). The microcentrifuge tube was inserted into the Micro Centrifuge Tube Thermomixer. Then, Au—$Fe_3O_4$ nanocomposites were synthesized by the same procedures to synthesize $Fe_3O_4$ nanoparticles. The final products washed with deionized water were stored in a refrigerator.

The similarities and differences of $Fe_3O_4$ nanoparticles and Au—$Fe_3O_4$ nanocomposites were observed with a JEOL 2100 TEM operated at 200 kV accelerating voltage and a Gatan Ultrascan 1000Xp digital camera.

Standards and Sample Containing Influenza A Virus Recombinant and ODI-CL Reagents Standards and samples were prepared in a bio-safety cabinet. Also, $H_2O_2$ in isopropyl alcohol and ODI in ethyl acetate were prepared in a fume hood.

Synthesis of Au—$Fe_3O_4$ Nanocomposite

Figure 7:
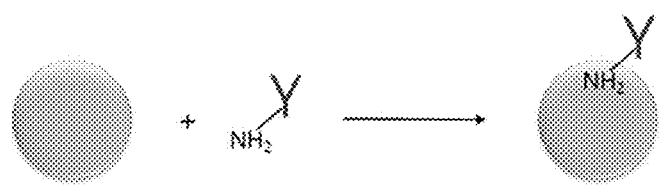
FIG. 7 illustrates the immobilization of H1N1 antibody on the surface of Au nanoparticle based on the electrostatic interaction between Au and antibody.

As shown in FIG. 7, it is possible to immobilize antibody on the surface of Au nanoparticle through the electrostatic interaction between Au nanoparticle and $NH_2$ of antibody. Using the method, H1N1 antibody cam be immobilized on the surface of Au nanoparticle.

Figure 8:
FIG. 8 is photos of (A) $Fe_3O_4$ nanoparticles, (B) Au—$Fe_3O_4$ nanoparticles.
Figure 8:
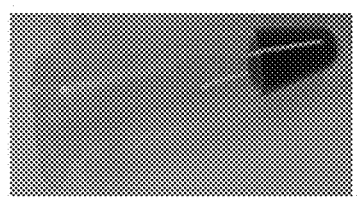
Figure 8:
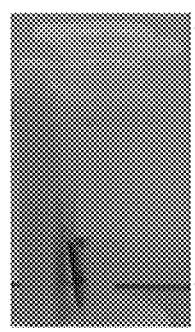
Figure 8:
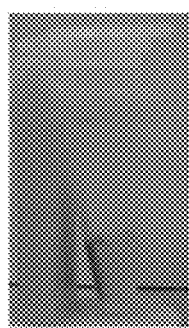

In order to develop an enzyme immunoassay capable of sensing H1N1, Au—$Fe_3O_4$ nanocomposites were synthesized. Also, $Fe_3O_4$ nanoparticles was synthesized to compare the similarity and difference between $Fe_3O_4$ nanoparticle and Au—$Fe_3O_4$ nanocomposites. As shown in FIG. 8, the color of solution containing $Fe_3O_4$ nanoparticles is black, whereas the solution containing Au—$Fe_3O_4$ nanocomposites is dark brown. It was possible to separate $Fe_3O_4$ nanoparticle and Au—$Fe_3O_4$ nanocomposites in solution using a magnetic bar. The time necessary for the separation of $Fe_3O_4$ was slightly faster than that of Au—$Fe_3O_4$ nanocomposites.

Figure 9:
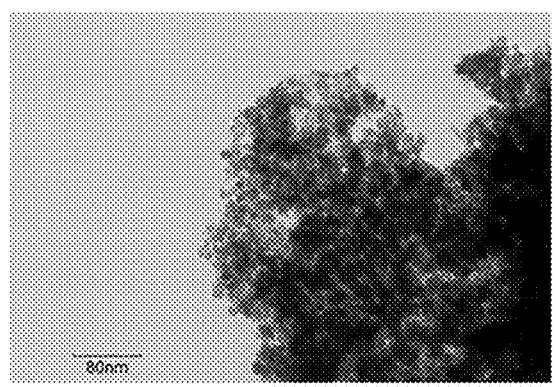
FIG. 9 shows TEM images of $Fe_3O_4$ nanoparticles (A) and Au—$Fe_3O_4$ nanocomposites (B).
Figure 9:
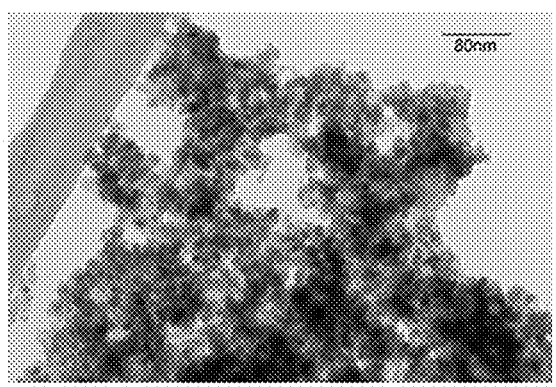
Figure 9:
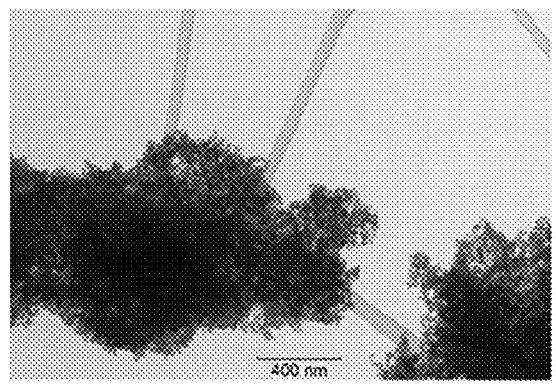
Figure 9:
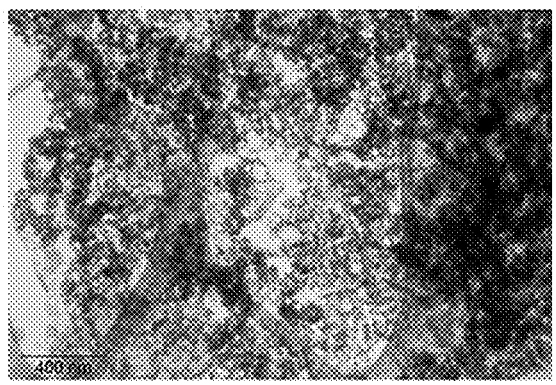

As shown in the TEM images of FIG. 9, $Fe_3O_4$ nanoparticles aggregate as a black cluster as shown in FIG. 9(A), whereas Au—$Fe_3O_4$ nanocomposites shown like the mixture of black and dark (or light) gray nanoparticles disperse widely.

Figure 10:
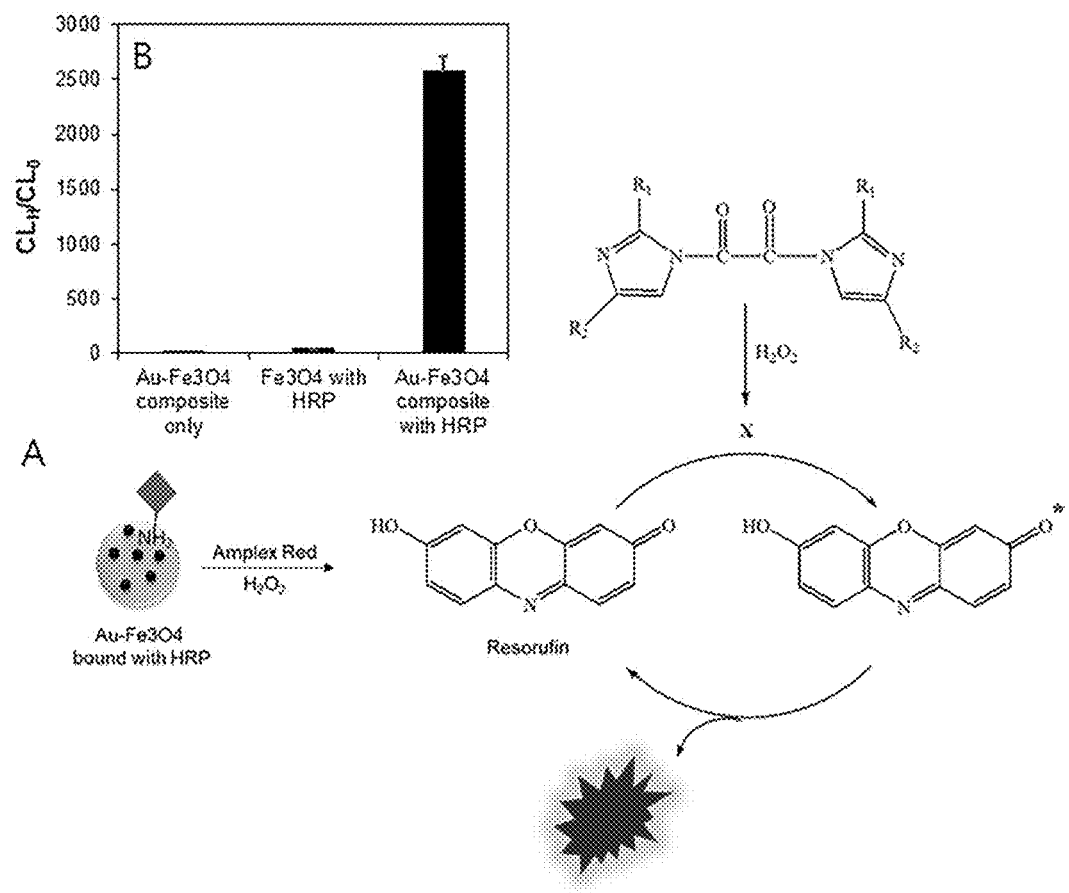
FIG. 10 shows (A) enzyme assay with ODI-CL detection using Au—$Fe_3O_4$ bound with HRP, (B) enzyme reactions of $Fe_3O_4$ bound with HRP and Au—$Fe_3O_4$ bound with HRP.

As shown in FIG. 10(A), Au—$Fe_3O_4$ bound with HRP can be used as an enzyme in the enzyme reaction for the analysis of $H_2O_2$ in a sample. Amplex Red, non-fluorescent compound, may be a substrate. When a certain concentration of $H_2O_2$ reacts with Amplex Red in the presence of Au—$Fe_3O_4$ bound with HRP, resorufin, fluorescent compound, is formed. Resorufin emits bright light in ODI-CL reaction based on the principle of the internal CRET between resorufin and X. As shown in FIG. 10(B), the $CL_H/CL_0$ in the presence of Au—$Fe_3O_4$ bound with HRP was about 2500-fold higher than that in the presence of Au—$Fe_3O_4$ nanocomposite only. $CL_H$ is the relative CL intensity measured in the presence of Au—$Fe_3O_4$ bound with HRP. $CL_0$ is the background measured in the presence of Au—$Fe_3O_4$ nanocomposite only. FIG. 10(B) also shows that $CL_H/CL_0$ in the presence of Au—$Fe_3O_4$ bound with HRP is about 60-fold larger than that in the presence of $Fe_3O_4$ bound with HRP. Based on the results shown in FIG. 10(B), it is confirmed that the role of Au in Au—$Fe_3O_4$ nanocomposite is to immobilize a specific antibody, whereas that of $Fe_3O_4$ in Au—$Fe_3O_4$ nanocomposite is to separate a biomarker bound with the antibody immobilized Au—$Fe_3O_4$ nanocomposite in a sample.

Enzyme Immunoassay with a H1N1 Antibody and ODI-CL Detection

Figure 11:
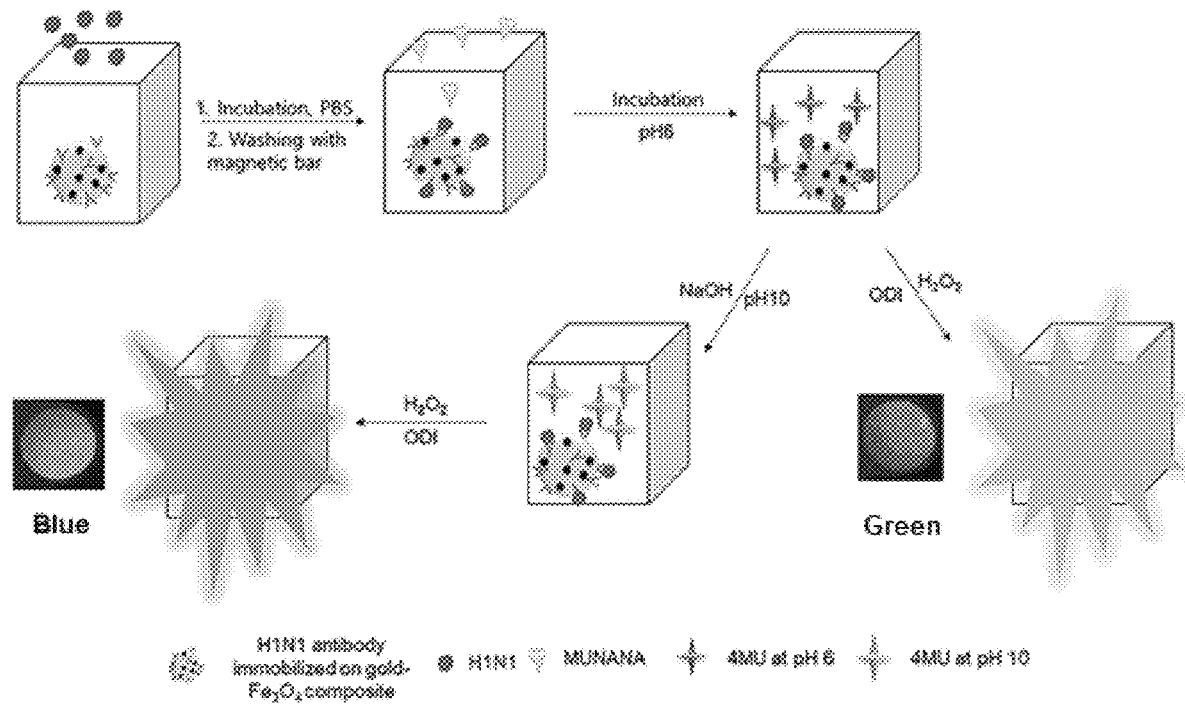
FIG. 11 illustrates the enzyme immunoassay with a single H1N1 antibody.

FIG. 11 shows the procedure of enzyme immunoassay with ODI-CL detection capable of quantifying trace levels of H1N1 in a sample. A sample containing H1N1 diluted in PBS was mixed with Au—$Fe_3O_4$ bound with H1N1 antibody in a well. The mixture was incubated for 1 hr at 37° C. After the incubation, H1N1 captured by antibody bound with Au—$Fe_3O_4$ nanocomposite was separated with a magnetic bar and washed 3 times with PBST. Then 0.5 mM MUNANA in phosphate buffer (pH 6) was added in the well for the reaction of MUNANA and H1N1 captured by antibody bound with Au—$Fe_3O_4$ nanocomposite for 10 min at room temperature. The relative CL intensity of 4MU formed from the reaction at pH 6 was measured with the luminometer. Also, 4MU in pH 10 with the addition of NaOH was prepared. The relative CL intensity of light emitted 4MU in the final solution was measured with the additions of $H_2O_2$ and ODI.

Figure 12:
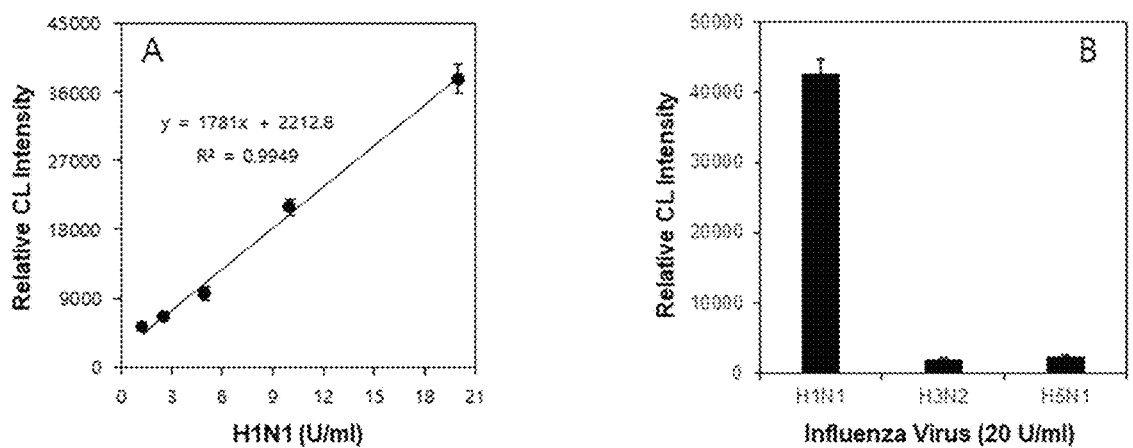
FIG. 12 shows (A) calibration curve for the quantification of H1N1 influenza A virus using the enzyme immunoassay operated with a single H1N1 antibody and ODI-CL detection, (B) the selectivity of enzyme immunoassay capable of sensing H1N1 influenza A virus.

As shown in FIG. 12(A), the enzyme immunoassay with ODI-CL detection can quantify trace levels of H1N1 with the calibration curve. The limit of detection (LOD=background+3σ) was as low as 0.19 U/ml. σ is the standard deviation for the average of the background that was measured 20 times.

FIG. 12(B) shows that the enzyme immunoassay with ODI-CL detection has good selectivity. The relative CL intensity in the presence of 20 U/ml H1N1 was about 20-fold higher than the background in the absence of H1N1. Also, the relative CL intensity in the presence of H3N2 (or H5N1, 20 U/ml each) was similar to the background within the statistically acceptable error range (<6%).

Based on the experimental results observed with the new enzyme immunoassay with ODI-CL detection, it is confirmed that the biosensor including an (capture) antibody only (e.g., hemagglutinin (HA) subtype antibody), can provide a cost-effective and rapid detection of the influenza A virus. The relative CL intensity measured with the present enzyme immunoassay, operated with a single antibody, may be proportionally enhanced with the increase of H1N1 in a sample. This is because NA of H1N1 bound with the antibody acts as an enzyme capable of converting MUNANA to 4MU.

With the development of enzyme assay (with ODI-CL detection), it is possible to devise a new enzyme immunoassay with a capture antibody immobilized on the surface of $Au-Fe_3O_4$ nanocomposite. This is because NA of H1N1 captured by the antibody bound with $Au-Fe_3O_4$ can react with MUNANA to produce 4MU. Thus, relative CL intensity was proportionally enhanced with the increase of H1N1 in a sample.

It is to be understood that the above-described biosensor and method are merely illustrative embodiments of the principles of this disclosure, and that other compositions and methods for using them may be devised by one of ordinary skill in the art, without departing from the spirit and scope of the invention. It is also to be understood that the disclosure is directed to embodiments both comprising and consisting of the disclosed parts.

What is claimed is:

1. A kit for detecting an influenza A virus in a sample, the kit comprising:
    a biosensor;
    a container;
    a sodium phosphate buffer for adjusting the pH between 5.5 to 6.5;
    a sodium hydroxide buffer for adjusting the pH between 9.3-11.3; and
    1,1'-oxalyldiimidazole chemiluminescence (ODI-CL) reagent,
    wherein the biosensor comprises an influenza A virus antibody immobilized on a surface of $Au-Fe_3O_4$ composite,
    wherein the antibody binds with the influenza A virus in the sample, which converts 4-methylumbelliferyl-N-acetyl-α-D-neuraminic acid (MUNANA) to 4-methyl umbelliferone (4-MU),
    wherein the 4-MU emits green light at pH of 5.5-6.5, and
    wherein the 4-MU emits blue light at pH of 9.3-11.3.

2. The kit of claim 1, wherein the 1,1'-oxalyldiimidazole chemiluminescence (ODI-CL) reagent comprises an ODI and $H_2O_2$.

3. A method of detecting an influenza A virus in a sample, comprising:
    immobilizing an influenza A virus antibody on a surface of $Au-Fe_3O_4$ composite;
    mixing the immobilized antibody with 4-methylumbelliferyl-N-acetyl-α-D-neuraminic acid (MUNANA), and incubating the mixture to form 4-methylumbelliferone (4-MU);
    adjusting pH of the incubated mixture between 5.5 to 6.5 and measuring light intensity derived from the 4-MU by using a first enzyme assay with 1,1'-oxalyldiimidazole chemiluminescence (ODI-CL) detection; and
    adjusting pH of the incubated mixture between 9.3-11.3 and measuring light intensity of derived from the 4-MU by using a second enzyme assay with 1,1'-oxalyldiimidazole chemiluminescence (ODI-CL) detection,
    wherein a sodium phosphate buffer is used for adjusting the pH between 5.5 to 6.5; and a sodium hydroxide buffer is used for adjusting the pH between 9.3-11.3.

4. The method of claim 3, wherein the first and second enzyme assays with 1,1'-oxalyldiimidazole chemiluminescence (ODI-CL) detection are performed by using ODI and $H_2O_2$.

5. The method of claim 3, wherein the influenza A virus antibody is a hemagglutinin (HA) subtype antibody.

6. The method of claim 3, wherein the influenza A virus is H1N1 type, H3N2 type or H5N1 type influenza A virus.

7. The method of claim 3, wherein the step of incubating the mixture is performed for 6-12 minutes at room temperature.

8. The kit of claim 1, wherein the sample is plasma or whole blood.

* * * * *